United States Patent [19]

Anuta

[11] 4,341,691

[45] Jul. 27, 1982

[54] LOW VISCOSITY BONE CEMENT

[75] Inventor: David A. Anuta, Winona Lake, Ind.

[73] Assignee: Zimmer, Inc., Warsaw, Ind.

[21] Appl. No.: 122,896

[22] Filed: Feb. 20, 1980

[51] Int. Cl.³ .................. C08F 265/06; C08J 3/20; C08K 7/04
[52] U.S. Cl. .................. 523/116; 128/92 C; 128/92 CA; 128/92 G; 128/92 R; 525/309; 524/495; 524/523; 524/533; 523/221
[58] Field of Search .............. 260/42.17, 42.52, 42.53; 525/309; 128/92 C, 92 CA, 92 G, 92 R

[56] References Cited

U.S. PATENT DOCUMENTS

| | | | |
|---|---|---|---|
| 3,223,083 | 12/1965 | Cobey .................. | 128/92 |
| 3,649,608 | 3/1972 | Logemann et al. ......... | 525/309 |
| 4,064,566 | 12/1977 | Fletcher et al. .......... | 260/42.17 |
| 4,093,576 | 6/1978 | de Wijn ................ | 128/92 C |
| 4,107,845 | 8/1978 | Lee, Jr. et al. ............ | 260/42.17 |
| 4,141,864 | 2/1979 | Rijke et al. .............. | 128/92 G |
| 4,282,140 | 8/1981 | Bousquet et al. .......... | 260/42.17 |

FOREIGN PATENT DOCUMENTS 1431211  4/1976  United Kingdom .
2009200  6/1979  United Kingdom .

OTHER PUBLICATIONS

Zimmer Product Brochure #1478, "A Sophisticated System to Improve Implant Fixation", 1980.

*Primary Examiner*—Allan Lieberman
*Attorney, Agent, or Firm*—R. H. Brink; M. L. Geringer

[57] ABSTRACT

An acrylic cement-like substance which permits seating and securing of a prosthesis into living bone which comprises a mixture of a liquid monomer component and a polymer powder component such that upon mixing the two components, a cement which maintains a low viscosity for a longer period of time is formed. The low viscosity bone cement is intended for syringe or injector gun use only as it is to be used before the cement becomes doughy. This low viscosity bone cement has a viscosity of approximately 20 degrees C. (68 degrees F.), of less than 1500 poise, and preferably less than 1000 poise up to the sixth or seventh minute after the two components are mixed. The cement used in the lower viscosity state is more capable of penetrating the trabeculae of bones when used to secure a prosthesis, than when the cement is applied in the doughy state.

21 Claims, 1 Drawing Figure

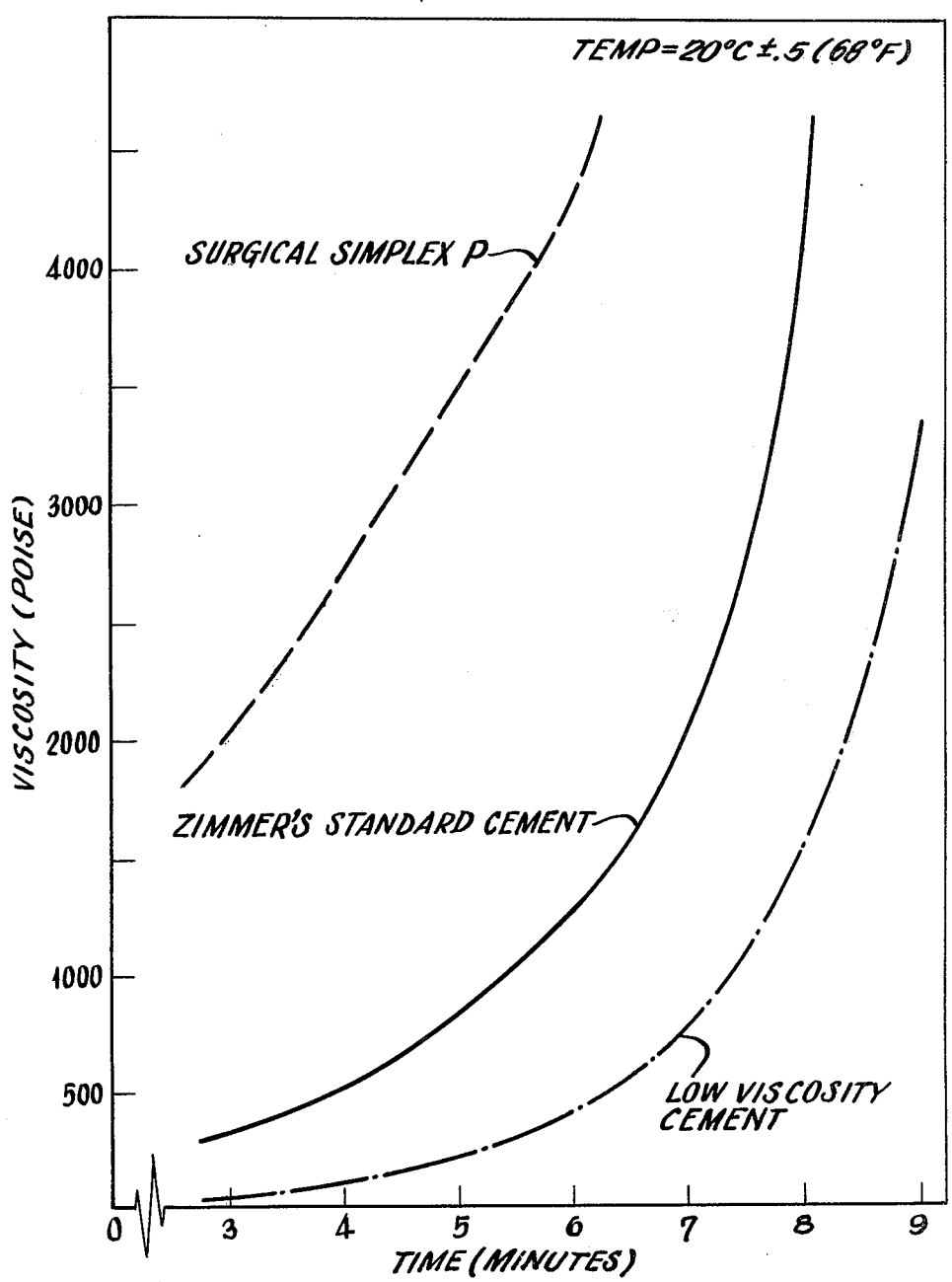

LOW VISCOSITY BONE CEMENT

BACKGROUND OF THE INVENTION

The present invention relates to improved surgical bone cement compositions and, more particularly, to a bone cement formulated for use in the low viscosity state, which enables the bone cement to penetrate the trabeculae of the bones when used to secure a prosthesis. This penetration allows a more secure interlock between the cement and the bone, and therefore there is less likely to be a failure at the bone/cement interface.

Various types of bone cements have been used for securing prostheses, but traditionally bone cements were applied digitally and therefore, it was necessary for the cement to have a doughy consistency during the time it was being applied (its working period). In the past few years, bone cement injectors have come into use. The problem often encountered is that the regular doughy cement is often too stiff to be easily extruded from the cartridge of a bone cement injector. Often the cement ends up hardening or setting up while still in the cartridge. And more important than this, the regular doughy cement does not effectively penetrate the trabeculae of bone to create a secure interlock. This leads to loosening and eventual failure of the implanted prosthesis.

Many existing bone cements consist of a liquid monomer component and a polymer powder component. Bone cements, such as ZIMMER ® Bone Cement sold by Zimmer USA, Inc. and SURGICAL SIMPLEX ® P sold by Howmedica, typically are comprised of a liquid component to powder component ratio of one to two (volume/weight) where the volume is in milliliters and the weight is measured in grams. When mixing the liquid and powder components, the liquid is added to the powder, not the powder to the liquid. The mixture is stirred until a dough-like mass is formed that does not stick or adhere to the rubber gloves of the operator. (This is considered the dough time.) The dough-like mass is then usually hand manipulated or kneaded to obtain a proper consistency for digital application of the cement to the bone. The cement is then applied by hand and then the prosthesis is inserted and positioned in the cement and maintained secure until the cement hardens. (This is called set time.) The viscosity of acrylic cements increases with time elapsed after mixing the monomer and polymer components. It starts out at a lower viscosity and progresses to a stiffer and stiffer mixture until it eventually hardens completely. This type of constantly changing viscosity is representative of a pseudoplastic material.

ASTM (American Society of Testing Materials) has a standard (ASTM F 451) for acrylic bone cements. In this standard, the doughing time and setting time for acrylic bone cements is standardly defined. These tests are performed at 23±2 degrees C. (72 degrees F.). To measure dough time, a stop watch is started at the onset of combining powder with the liquid. The mixture is gently probed with a surgically gloved finger. In early stages of probing, it is visually noted that fibers are formed between the surface of the mix and the finger as it leaves the surface. The time at which it is first observed that the gloved finger separates clearly is known as the dough time.

The set time according to ASTM standards is also tested at 23±2 degrees C. The temperature of the cement is recorded continuously again with time measured from the onset of mixing the powder and the liquid. Set time, according to ASTM standards, is the time at which the temperature of the mixture equals $(T_{max}+T_{ambient})/2$. $T_{max}$ equals maximum temperature reached. $T_{ambient}$ equals the ambient temperature of 23±2 degrees C. The set time is considered to be the time at which the mixture hardens.

Injector guns have been advocated for application of bone cement, especially in cavities such as the femoral canal, because long slender injector tips are useful for inserting the cement deep into the cavity, instead of trying to apply it by hand. Gun application also reduces the tendency to form laminations and voids in the cement and also reduces the inclusion of blood into the cement. The problem with existing cements is that they were formulated for digital use and were therefore formulated to use after dough time when the cement becomes stiff enough to handle. In order to use the standard cements in injector guns, the surgeon must attempt to extrude the cement before dough time (the time when the cement mixture does not stick or adhere to the rubber gloves of the operator), because by then the cement is getting relatively stiff. Also, by the time the cement reaches dough time, the cement will not as effectively penetrate the trabeculae of the bone to form the desired cement/bone interlock, which is the sole mechanism for anchoring implanted prostheses securely to living bone.

ASTM has a maximum dough time specified for acrylic bone cements of five minutes. This five-minute maximum again is measured at 23 degrees C. Temperatures in operating rooms are often cooler than 23 degrees C., and are often at approximately 20 degrees C. or 68 degrees F. Once the cement powder and liquid are mixed, the reaction proceeds at a slower rate at a cooler temperature. Therefore, typically dough time occurs about a minute or so later in the operating room (O.R. dough time) than under standard ASTM test conditions.

Zimmer's standard bone cement is targeted for an ASTM dough time of about 1½ to 2 minutes. The O.R. dough time would then be approximately at 2½ to 3 minutes from the onset of mixing. Actual mixing of the powder and liquid usually takes about one minute. This leaves only 1½ to 2 minutes to finish preparing the bone cement injector and extruding the bone cement in order to use it before O.R. dough time. Other existing acrylic bone cements typically have a comparable O.R. dough time of about three minutes or less. By dough time, the cement is becoming stiff enough that it becomes difficult to extrude the cement from the cartridge and tip. Problems are often encountered when using the cement in injector guns in this doughy, more viscous state, but it is attempted. The potential for secure fixation is less than optimal under these circumstances. As stated before, the cement often ends up becoming too stiff to extrude and often ends up hardening in the cartridge. Needless to say, this is undesirable and very risky under operating room conditions.

Another type of bone cement is disclosed in U.S. Pat. No. 4,064,566 which describes a graphite fiber reinforced cement. The patent speaks of preparing a slurry of the polymer powder in the liquid monomer and then adding the graphite fibers and curing agents to the mixture. The graphite fibers strengthen and reinforce the cement. The patent indicates that the fibers are added at the time the polymer and monomer components are ultimately mixed, and does not indicate that the fibers are pre-mixed in the polymer powder.

OBJECTS OF THE INVENTION

A principal object of this invention is to provide an acrylic cement for securing a prosthesis to living bone which maintains a low viscosity for a longer period of time (has a longer dough time) than standard pseudoplastic cements which allows the cement to be used in the low viscosity state such that the cement penetrates into the trabeculae of living bone to create a secure interlock at the cement/bone interface, and yet still has the strength characteristics of standard bone cements.

A further object of this invention is to provide a bone cement which is more suitable for use in bone cement injector guns, such that it is fluid enough to flow easily through the cartridge and tips without too much resistance for a reasonable length of time in order to prevent the previous problems of clogged injector tips, hard to extrude cement, split cartridges from too much pressure, and hardening or setting up of the cement before it is extruded from the cartridge and tip.

A still further object of this invention is to provide a bone cement that maintains a viscosity at approximately 20 degrees C. (68 degrees F.), of less than 1500 poise, and preferably less than 1000 poise up to the sixth or seventh minute after the polymer and monomer components are mixed.

A still further object of the invention is to provide a bone cement in which, while it is less viscous than regular standard bone cements, it sets up or ultimately hardens within a reasonable amount of time since the prosthesis must be maintained in position securely without movement until the cement has hardened and the prosthesis is firmly fixed.

A still further object of the invention is to provide a low viscosity bone cement which is adaptable to include a dispersion of high modulus graphite fibers for reinforcing the strength of the bone cement, yet retaining the low viscosity advantages and characteristics of the bone cement disclosed by this invention, and further is capable of having the fibers pre-mixed in the powder component for large scale production.

SUMMARY OF THE INVENTION

The low viscosity cement of this invention achieves all of the above stated objects of invention, and has proven to be very effective in testing and recent clinical use. The bone cement of this invention permits seating and securing of prosthesis into living bone and is comprised of a liquid monomer and a polymer powder component. The polymer powder particles are conventionally referred to as beads, and will be referred to as polymer beads or polymer powder beads hereinafter. The bone cement of this invention is able to maintain a low viscosity for a longer period of time because the polymer bead mixture has less overall surface area than other polymer powder mixtures. The cement of this invention, achieves a consistency after mixing the polymer powder with the liquid monomer that has a viscosity at approximately 20 degrees C. (68 degrees F.) of less than 1500 poise, and preferably less than 1000 poise, up to the sixth or seventh minute after mixing.

For the purpose of this application, viscosity measurements will be noted at 68 degrees F. This is a typical temperature for taking viscosity measurements. It is to be noted, though, that there is a drastic difference between viscosity responses at different temperatures. As noted before, the curing reaction of the bone cement mixture proceeds faster at a higher temperature. Therefore, for example, viscosity measurements with respect to time would be much higher (stiffer) if done at 72 degrees F. than if done at 68 degrees F.

The polymer bead mixture in the powder component of the present invention is comprised of a mixture of 85–95% polymer beads (which will be referred to as regular beads) with a maximum average size of 25 microns, and 5–15% of the polymer beads which have been milled. Milled beads are put in a milling machine which roughens and breaks up their surface. This allows more of their surface area to be exposed for the reaction. As an alternative to milling this portion of the polymer beads, they can be sifted through mesh screens to a size range of less than 13 to 17 microns. Likewise, these sifted polymer beads whose size range is less than 13 to 17 microns will behave in a similar fashion to larger beads which have been milled, due to the increased surface area of the milled beads.

The total powder component is comprised of 80–100% by weight of the polymer bead mixture described above plus barium sulfate U.S.P. to make the mixture radiopaque and benzoyl peroxide which is a catalyst. An important factor in the low viscosity bone cement of this invention is that it has a longer dough time than existing bone cements, and hence allows a longer working time for injector use, and yet it still sets up in less than eleven minutes after initial mixing of the powder and liquid components.

BRIEF DESCRIPTION OF THE DRAWING

FIG. 1 illustrates a representative graph of viscosity versus time, comparing the relative viscosity of Zimmer's standard bone cement, SURGICAL SIMPLEX ® P sold by Howmedica, Inc. and the new low viscosity formulation of this invention as a function of time. For the graph, time is measured from the onset of mixing the powder and liquid components. This graph illustrates the time span from three minutes to nine minutes after the onset of mixing.

DETAILED DESCRIPTION OF THE INVENTION

The acrylic cement-like substance described here is comprised of a liquid monomer component and a polymer powder component. The liquid monomer used in the particular embodiment described here is methyl methacrylate monomer, and the polymer powder is poly methyl methacrylate.

The acrylic cement of this invention utilizes the same liquid component to powder component ratio as Zimmer's standard (regular) bone cement. That ratio is one to two (volume/weight) where the liquid component is measured in milliliters and the powder component is measured in grams. For example, when mixing the cement, one could add 20 ml of liquid monomer to 40 grams of polymer powder for a properly mixed dosage.

The composition of the liquid monomer component of the low viscosity bone cement is identical to the composition of the liquid monomer component of Zimmer's standard bone cement. It is comprised of the following:

96.2 to 98.3% (by volume) methyl methacrylate monomer, preferably 97.25%;

2.5 to 3.0% (by volume) N, N-dimethyl-p-toluidine, preferably 2.75%; and

75±10 ppm of Hydroquinone.

The N, N-dimethyl-p-toluidine is added to promote cold curing when the two components (liquid monomer component and polymer powder component) are mixed. Hydroquinone is added to prevent premature polymerization which may occur under conditions such as heat, light or chemical reagents. The formula for the methyl methacrylate monomer is:

$$CH_2=\underset{\underset{CH_3}{|}}{C}-COOCH_3$$

The overall proportions of the composition of the polymer powder component are generally equivalent to Zimmer's standard bone cement, but the make-up of the poly methyl methacrylate powder within the total powder component is different. Overall, both Zimmer's standard cement and the modified low viscosity cement have the following composition for the total powder component:

80 to 100% (by weight) poly methyl methacrylate, preferably 89.25%;

9.0 to 11.0% (by weight) barium sulfate, U.S.P., preferably 10.0%;

0.5 to 1.0% (by weight) benzoyl peroxide, preferably 0.75%, and a maximum of 1.0% moisture by weight.

The barium sulfate (BaSO$_4$) is optional, but provides radiopacity to the formulation so that the cement is visible in X-rays. The benzoyl peroxide acts as a catalyst when the monomer component and polymer component are mixed. The formula for the poly methyl methacrylate is:

$$\left(-CH_2-\underset{\underset{COOCH_3}{|}}{\overset{\overset{CH_3}{|}}{C}}-CH_2-\underset{\underset{COOCH_3}{|}}{\overset{\overset{CH_3}{|}}{C}}-CH_2-\underset{\underset{COOCH_3}{|}}{\overset{\overset{CH_3}{|}}{C}}-\right)_n$$

The difference in the modified low viscosity bone cement lies mainly in the make-up of the poly methyl methacrylate powder within the powder component.

The poly methyl methacrylate powder in Zimmer's standard bone cement is comprised of a mixture of 65 to 70% polymer beads with a maximum average size of 25 microns, (regular beads), and 30 to 35% of the polymer beads which have been milled. Zimmer's modified low viscosity bone cement is comprised of 85 to 95%, preferably 90%, of the regular polymer beads, and 5 to 15%, preferably 10%, of the beads which have been milled. Using the appropriate poly methyl methacrylate bead mixture for the modified low viscosity cement in the polymer component mixed with the monomer component results in a bone cement with a viscosity, at approximately 20 degrees C. (68 degrees F.) of less than 1500 poise, and preferably less than 1000 poise up to the sixth or seventh minute after the powder and liquid components are initially mixed.

In order to further specify the make-up of the regular beads and milled beads, they will be discussed in terms of particle size. Both regular beads and milled beads must fall through a #40 mesh sieve screen (a 425 micron opening). Then all of the regular beads must additionally fall through a 100 mesh screen (a 150 micron opening). These beads are used in the regular bead mixture. The beads which fell through the 40 mesh screen, but did not fall through the 100 mesh screen are to be used for the milled bead mixture. This fraction of beads is put into a milling machine which roughens and breaks up their surface. This allows more surface area to be exposed than would be exposed on a substantially spherical bead of comparable size which was not milled.

As an alternative to milling the "non-regular" bead portion, these polymer beads can be sifted through mesh screens to a size range of less than 13 to 17 microns. This sifted "non-regular" polymer bead portion will behave in a similar manner to larger beads which have been milled, due to the increased surface area of the milled beads from the milling operation.

A typical size range for the bead fraction which fell through the 40 mesh and 100 mesh screens (regular bead fraction) would be as follows:

2.7% beads less than 150 microns, but greater than 106 microns.

6.8% beads less than 106 microns, but greater than 75 microns.

17.3% beads less than 75 microns and greater than 45 microns.

71.0% beads less than 45 microns and greater than 13 to 17 microns.

2.2% beads less than 13 to 17 microns. It has been previously stated that the regular beads have a maximum average size of 25 microns. It can be seen from the above typical size range for the regular bead fraction that only approximately 2.2% of the beads are less than 13-17 microns, with 97.8% of the beads being greater than 13-17 microns. The majority of those beads (71% in the sample typical range indicated above) are less than 45 microns and greater than 13-17 microns. Therefore, it can be seen that since such a small fraction (2.2%) of the typical size range for the regular bead fraction is less than 13-17 microns, and 97.8% is greater than 13-17 microns, that the average bead size would not be less than 13-17 microns. Hence, it would follow that a minimum average size of 13 microns for the regular bead size would be appropriate.

A typical size range for the milled bead fraction would be as follows:

3.5% beads less than 425 microns, but greater than 106 microns.

6.0% beads less than 106 microns, but greater than 75 microns.

25.1% beads less than 75 microns and greater than 45 microns.

56.1% beads less than 45 microns and greater than 13 to 17 microns.

7.9% beads less than 13 to 17 microns.

Although the regular bead fraction actually has a larger percentage of smaller beads, (less than 45 microns), the milled bead fraction still overall exposes more surface area because the shape and surface geometry of the beads are so irregular and roughened up from the milling operation, as compared to the regular beads which are substantially spherical.

Alternately, a bead fraction, where the bead powder is sifted to a size range of less than 13 to 17 microns can be substituted for the milled bead fraction, and will impart characteristics similar to the above-described milled bead fraction.

A representative viscosity/time curve is shown in FIG. 1 illustrating typical viscosity trends for Zimmer's standard bone cement, Howmedica's SURGICAL SIMPLEX ® P, and the new low viscosity formulation.

The measurements were taken at 20±0.5 degrees C. (68 degrees F.) often a typical operating room temperature. Note that at the sixth minute after mixing, which is done at time 0, the low viscosity cement shows a viscosity of approximately 400 poise. At the seventh minute, the viscosity is still less than 1000 poise, graphically illustrated at about 750 poise. In contrast, note that Zimmer's standard cement has already reached 1500 poise by the sixth minute and is above 2000 poise by the seventh minute. This trend is also true for SURGICAL SIMPLEX ® P as indicated on the graph, as well as for all other commercially available acrylic cements formulated for hand or digital applications. Although other acrylic cements have varying viscosity curves, all other commercial acrylic bone cements of which the inventor is aware, have viscosities measured at 68 degrees F. which are greater than 1500 poise by the sixth minute after mixing.

It is to be noted that there is a definite correlation between dough time and viscosity. A bone cement which has a longer dough time, therefore also maintains a lower viscosity for a longer period of time than a cement with a relatively short dough time. As was previously explained in the Background of the Invention, Zimmer's standard bone cement typically has an ASTM dough time of about 1½ to 2 minutes, and an operating room (O.R.) dough time of about 2½ to 3 minutes. Existing acrylic bone cements typically have a comparable or even shorter dough time than this.

The low viscosity cement of the present invention is formulated to have an ASTM dough time of approximately 4¾ minutes, and therefore under typical operating room conditions, it would have an O.R. dough time of approximately 5¾ minutes, or almost 6 minutes. If it takes one minute from onset of mixing the powder and liquid components to mix the cement, this would still allow at least 4¾ minutes to finish preparing the bone cement injector for use and extruding the bone cement from the injector, whereas other existing bone cements only allow about 2 minutes in which to do this work before they start becoming too stiff to be effective for injector use and also too stiff to penetrate into the trabeculae of bone. Therefore, the new low viscosity formulation allows more than twice as much operating room time to effectively use bone cement with an injector gun, as well as extends the time during which intrusion into the interstices of trabecular bone can be accomplished.

Dough time is a function of the surface area of the polymer powder. The greater the total surface area available, the shorter the dough time. Therefore, Zimmer's standard bone cement has a shorter dough time than the modified low viscosity cement, since the standard cement has a larger percentage of milled beads in the polymer powder and hence more surface area than the modified low viscosity cement. Since other acrylic cements don't all use milled polymer beads in their mixtures, it is to be understood that a lower viscosity cement could still be achieved by decreasing the total surface area of the polymer powder, or increasing the average polymer bead size.

In formulating a lower viscosity bone cement it is important that the bone cement still sets up in a reasonable amount of time. After the cement has been injected and the prosthesis inserted and/or positioned in place, it must be maintained securely without movement until the cement sets up or completely hardens to fix the prosthesis firmly in place. The maximum allowable set time for acrylic cements is 15 minutes. But if the surgeon has finished extruding the bone cement by the sixth minute and places the prosthesis in place in the cement in the next minute, the prosthesis would have to be maintained in position for eight more minutes, which would be unreasonable and also difficult to do. By adjusting the levels of catalyst such as benzoyl peroxide, present in the powder component, a reasonable set time can still be maintained.

Zimmer's standard cement as well as the new low viscosity cement are both formulated to have a set time from 7 to 10½ minutes after initial mixing. Therefore, with low viscosity cement, the prosthesis would potentially only have to be maintained in position for less than a minute or at the maximum, three to four minutes. This is important to note because, in making a cement which maintains a low viscosity for a longer period of time, it is probable that some formulation attempts would just completely slow down the curing process and create a runny cement which didn't set up effectively. Therefore, maintaining a set time is essential in formulating a low viscosity cement.

When polymerization of the cement mixture is complete, the cement is a buffer for even weight distribution and other stresses between the prosthesis and bone. When the cement is injected in the lower viscosity state, the interlock between the bone and the cement is much stronger because the low viscosity allows the cement to penetrate the trabeculae of the bone which are porous holes in the cancellous bone.

The lower viscosity cement as described, achieves a minimum compressive strength of 10,000 psi, which is comparable to other cements.

A further embodiment of the low viscosity bone cement further includes in the polymer powder component a dispersion of 1.8 to 2.2%, preferably 2%, by weight of high modulus graphite fibers. The proportion of liquid component and total powder component is still one to two (volume/weight) where the volume of liquid is in milliliters and the weight of the powder is in grams. The composition of the liquid monomer contains the same proportions of methyl methacrylate monomer, N, N-dimethyl-p-toluidine and hydroquinone as previously stated for the regular modified low viscosity bone cement.

The polymer powder within the powder component of the carbon reinforced embodiment still contains a ratio of 85 to 95% regular polymer beads and 5 to 15% of the polymer beads which have either been milled or sifted to a size range of less than 13 to 17 microns, although with this carbon reinforced embodiment, the ratio tends to be closer to the 90 to 95% regular beads and 5 to 10% of the other bead fraction. Utilizing the above polymer powder composition, the proportions of elements contained in the total polymer powder component are as follows:

80 to 100% (by weight) poly methyl methacrylate, preferably 87.25%.

9 to 11% (by weight) barium sulfate, U.S.P., preferably 10%.

1.8 to 2.2% (by weight) high modulus graphite fibers, preferably 2%.

0.5 to 1.0% (by weight) benzoyl peroxide, preferably 0.75% and a maximum of 1.0% moisture by weight.

Therefore, the carbon fibers represent approximately 2% of the total weight of the powder component. The length of the fibers used ranges from 0.79 to 7.14 millimeters (1/32 of an inch to 9/32 of an inch). The cross-sectional shape of the fibers could be described as dog-bone or figure eight shaped. Therefore, the fibers have a major and a minor diameter. The major diameter is approximately 15 microns and the minor diameter is approximately 6 microns. These dog-bone shaped carbon fibers are of a type which can be purchased from the Great Lake Carbon Corporation. The preferred type of carbon fiber used is called Fortafil, although others which are substantially equivalent may be used.

It is to be noted that the carbon reinforcing fibers are mixed into the dry powder component. This allows the fibers to be pre-mixed and packaged with the powder component. This is a contrast to the method described in U.S. Pat. No. 4,064,566 in which the liquid and powder components are mixed into a slurry and the carbon reinforcing fibers are added to the slurry. With this method, the fibers aren't being added until the bone cement is being mixed for use. With pre-mixing of the fibers in the powder component, the fibers can be more uniformly mixed and it saves the physician from trying to mix the fibers and distribute them uniformly in the mixture. Pre-mixing of the fibers in the powder is more effective and efficient with large scale production of the product.

The carbon reinforced low viscosity cement utilizing the above composition, still results in a bone cement with viscosity characteristics similar to the previous embodiment of the invention described, such that at 20 degrees C. (68 degrees F.), the viscosity is less than 1500 poise up to the sixth or seventh minute after the powder and liquid components are mixed, and preferably less than 1000 poise up to the sixth or seventh minute after mixing. This cement is reinforced for strength with the carbon fibers, and yet it still has the advantages of the low viscosity cement such as penetrating the trabeculae of the bone for a more effective bone/cement interlock, and working effectively and easily with the use of a bone cement injector gun for a longer period of time.

The invention described here is a low viscosity bone cement which is able to effectively penetrate the trabeculae of the bone in order to create stronger interface between the cement and bone when seating and securing a prosthesis into living bone with cement. The low viscosity cement described here also facilitates the use of bone cement injector guns without the problems encountered when attempting to use cements with shorter dough times (which would get stiffer more quickly) in an injector gun. This lower viscosity cement is not meant for digital application, but is specifically for use with an injector gun or syringe. While this invention has been described and exemplified in terms of its preferred embodiment, those skilled in the art can appreciate that modifications can be made without departing from the spirit and scope of this invention.

What is claimed is:

1. An acrylic bone cement composition comprising: a liquid monomer component and a polymer powder component in the form of beads wherein the liquid component to powder component ratio is 1 to 2 (volume weight) there the liquid component is measured in milliliters and the powder component is measured in grams and wherein said liquid monomer component is comprised of methylmethacrylate monomer and said polymer powder component is comprised at least 80% by weight of polymethylmethacrylate polymer powder in which at least 85-95% by weight of the polymethylmethacrylate polymer powder beads are regular beads which fall through a #40 mesh (425 micron openings) screen and a #100 mesh screen (150 micron openings) and which have a maximum average size of about 25 microns and a minimum average size of about 13 microns, and about 5-15% by weight of polymethylmethacrylate polymer powder beads which fall through a #40 mesh (425 micron openings) screen, but not through a #100 mesh screen, (150 micron openings) and are subsequently milled to roughen and break up the surface of the bead, and whereby when the liquid monomer component is mixed with said polymer powder component, the resulting cement has a viscosity of less than 1500 poise at approximately 20 degrees C. (68 degrees F.) for at least six minutes after the components are initially mixed, and such that the resulting bone cement becomes completely hard in not more than ten to eleven minutes from the time the components were initially mixed.

2. An acrylic cement as described in claim 1, wherein the polymer powder is comprised of a mixture of 90% regular polymer beads and 10% of said polymer beads which have been milled.

3. An acrylic cement as described in claim 1, wherein the liquid monomer component is comprised of 96.2 % to 98.3% by volume of methyl methacrylate monomer, and 2.5% to 3.0% by volume of N,N-dimethyl-p-toluidine.

4. An acrylic cement as described in claim 3, wherein the liquid monomer component further includes 75±10 ppm of hydroquinone.

5. An acrylic cement as described in claim 1, wherein the powder component is comprised of 80 to 100% by weight of the poly methyl methacrylate bead mixture and 0.5 to 1.0% by weight of benzoyl peroxide, a catalyst, and wherein the powder component allows for a maximum of 1% by weight moisture content.

6. An acrylic cement as described in claims 1 or 5, wherein the polymer powder component further includes 9.0 to 11.0% by weight of barium sulfate, U.S.P. to provide radiopacity to the cement.

7. An acrylic cement as described in claim 1, wherein the polymer powder component further includes a dispersion of 1.8 to 2.2% by weight of high modulus graphite fibers, wherein the cross-section of said fibers is substantially dog-bone shaped and has a major and minor diameter, wherein the major diameter is approximately 15 microns and the minor diameter is approximately 6 microns, and wherein said fibers have a length of approximately 0.79 to 7.14 millimeters.

8. An acrylic cement as described in claim 7, wherein the liquid monomer component is comprised of the proportions as stated in claim 3.

9. An acrylic cement as described in claim 7, wherein the powder component is comprised of 80 to 100% by weight of the poly methyl methacrylate bead mixture, 1.8 to 2.2% by weight of high modulus carbon fibers, and 0.5 to 1.0% by weight of benzoyl peroxide, a catalyst, and allows for a maximum of 1% by weight moisture content.

10. An acrylic cement as described in claims 7 or 9 wherein the polymer powder component further includes 9 to 11% by weight of barium sulfate, U.S.P. to provide radiopacity to the cement.

11. An acyrlic bone cement composition comprising: a liquid monomer component and a polymer powder component in the form of beads wherein the liquid component to powder component ratio is 1 to 2 (volume/weight) where the liquid component is measured in milliliters and the powder component is measured in grams and wherein said liquid monomer component is comprised of methylmethacrylate monomer and said polymer powder component is comprised at least 80% by weight of poly methylmethacrylate polymer powder in which at least 85-95% by weight of the poly methylmethacrylate polymer powder beads are regular beads which fall through a #40 mesh (425 micron openings) screen and a #100 mesh screen (150 micron openings) and which have a maximum average size of about 25 microns and a minimum average size of about 13 microns, and about 5-15% by weight of poly methylmethacrylate polymer powder beads which are less than 13 to 17 microns in diameter, and whereby when the liquid monomer component is mixed with said polymer powder component, the resulting cement has a viscosity of less than 1500 poise at approximately 20 degrees C. (68 degrees F.) for at least six minutes after the components are initially mixed, and such that the resulting bone cement becomes completely hard in not more than ten to eleven minutes from the time the components were initially mixed.

12. An acrylic cement as described in claim 11, wherein the polymer powder is comprised of a mixture of 90% regular polymer beads and 10% of said polymer beads which are less than 13 to 17 microns in diameter.

13. An acrylic cement as described in claim 11, wherein the liquid monomer component is comprised of 96.2% to 98.3% by volume of methyl methacrylate monomer, and 2.5% to 3.0% by volume of N, N-dimethyl-p-toluidine.

14. An acrylic cement as described in claim 13, wherein the liquid monomer component further includes 75±10 ppm of hydroquinone.

15. An acrylic cement as described in claim 11, wherein the powder component is comprised of 80 to 100% by weight of the poly methylmethacrylate bead mixture and 0.5 to 1.0% by weight of benzoyl peroxide, a catalyst, and wherein the powder component allows for a maximum of 1% by weight moisture content.

16. An acrylic cement as described in claims 11 or 15, wherein the polymer powder component further includes 9.0 to 11.0% by weight of barium sulfate, U.S.P. to provide radiopacity to the cement.

17. An acrylic cement as described in claim 11, wherein the polymer powder component further includes a dispersion of 1.8 to 2.2% by weight of high modulus graphite fibers, wherein the cross-section of said fibers is substantially dog-bone shaped and has a major and minor diameter, wherein the major diameter is approximately 15 microns and the minor diameter is approximately 6 microns, and wherein said fibers have a length of approximately 0.79 to 7.14 millimeters.

18. An acrylic cement as described in claim 17, wherein the liquid monomer component is comprised of the proportions as stated in claim 3.

19. An acrylic cement as described in claim 17, wherein the powder component is comprised of 80 to 100% by weight of the poly methylmethacrylate bead mixture, 1.8 to 2.2% by weight of high modulus carbon fibers, and 0.5 to 1.0% by weight of benzoyl peroxide, a catalyst, and allows for a maximum of 1% by weight moisture content.

20. An acrylic cement as described in claims 17 or 19, wherein the polymer powder component further includes 9 to 11% by weight of barium sulfate, U.S.P. to provide radiopacity to the cement.

21. An acrylic cement as described in claims 1 or 11, wherein the viscosity of the resulting bone cement after mixing is less than 1000 poise at approximately 20 degrees C. (68 degrees F.) for at least six minutes after the components are initially mixed.

* * * * *